United States Patent [19]

Roper

[11] Patent Number: 4,562,294

[45] Date of Patent: * Dec. 31, 1985

[54] SPIROKETONE PROCESS

[75] Inventor: Jerry M. Roper, Baton Rouge, La.

[73] Assignee: Ethyl Corporation, Richmond, Va.

[ * ] Notice: The portion of the term of this patent subsequent to Oct. 30, 2001 has been disclaimed.

[21] Appl. No.: 660,859

[22] Filed: Oct. 15, 1984

[51] Int. Cl.$^4$ .............................................. C07C 45/45
[52] U.S. Cl. ...................................... 568/362; 568/322
[58] Field of Search ....................... 564/395, 401, 389; 568/362, 347, 349, 322

[56] References Cited

U.S. PATENT DOCUMENTS 4,480,133 10/1984 Roper .................................. 568/362

OTHER PUBLICATIONS

Hatchard, J.A.C.S., vol. 80, pp. 3640–3642 (1958).
McClure, J. Org. Chem., vol. 27, pp. 2365–2368 (1962).

*Primary Examiner*—James H. Reamer
*Attorney, Agent, or Firm*—Donald L. Johnson; John F. Sieberth; Patricia J. Hogan

[57] ABSTRACT

Spiro[5.5]undeca-1,4,8-trien-3-ones are prepared by heating a reaction mixture consisting essentially of a 4-aminomethylphenol, a conjugated diene, and an inert solvent at a temperature of at least about 190° C.

12 Claims, No Drawings

SPIROKETONE PROCESS

FIELD OF INVENTION

This invention relates to spiroketones and more particularly to a process for preparing them.

BACKGROUND

Spiro[5.5]undeca-1,4,8-trien-3-ones are known compounds that are described in Hatchard, *Journal of the American Chemical Society*, Vol. 80, pp. 3640-3642 (1958); McClure, *Journal of Organic Chemistry*, Vol. 27, pp. 2365-2368 (1962); and copending application Ser. No. 472,196, filed Mar. 4, 1983, in the name of Jerry M. Roper (Roper). As taught in Roper, such spiroketones are of interest as antioxidants and/or as flame retardant, insecticide, or pharmaceutical intermediates; and they can be prepared by reacting a 4-aminomethylphenol with a conjugated diene and an alkyl halide, typically at a temperature in the range of about 50°-200° C., in an inert solvent. Roper also teaches that (1) his reaction proceeds via alkylation of the phenol reactant to a quaternary ammonium salt which subsequently forms a quinone methide that then undergoes cycloaddition with the diene and (2) the use of at least one molar equivalent of the alkyl halide is required in his process.

SUMMARY OF INVENTION

An object of this invention is to provide a novel process for preparing spiro[5.5]undeca-1,4,8-trien-3-ones.

Another object is to provide such a process which can be accomplished without the aid of an alkyl halide.

These and other objects are attained by heating a reaction mixture consisting essentially of a 4-aminomethylphenol, a conjugated diene, and an inert solvent at a temperature of at least about 190° C. so as to form a spiro[5.5]undeca-1,4,8-trien-3-one.

DETAILED DESCRIPTION

4-Aminomethylphenols utilizable in the practice of the invention include substituted and unsubstituted 4-aminomethylphenols. They are generally compounds corresponding to the formula:

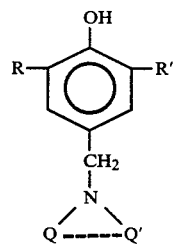

wherein R and R' are independently selected from hydrogen and hydrocarbyl groups containing 1-40 carbons; and Q and Q', when separate, are independently selected from hydrogen and hydrocarbyl groups containing 1-20 carbons and, when joined together, form a ring with the nitrogen to which they are attached, generally a five- or six-membered ring. Such compounds include, e.g., 4-aminomethylphenol; 2-methyl-, 2-ethyl-, 2-isopropyl-, 2-t-butyl-, 2-octyl-, 2-methyl-6-isopropyl-, 2-methyl-6-t-butyl-, 2-ethyl-6-t-butyl-, 2,6-dimethyl-, 2,6-diethyl-, 2,6-diisopropyl-, 2,6-di-secbutyl-, 2,6-di-t-butyl-, 2,6-diheptyl-, and 2,6-dioctyl-4-aminomethylphenols; the corresponding N-methyl-, N,N-dimethyl-, N,N-diethyl-, N,N-dioctyl-, N-ethyl-N-methyl-, and N-octyl-N-methyl-4-aminomethylphenols; 3,5-di-t-butyl-4-hydroxybenzylpiperidine; 3,5-di-t-butyl-4-hydroxybenzylmorpholine; 3,5-di-t-butyl-4-hydroxybenzylpyrrolidine, etc. The compounds that are preferred vary with the particular end products desired but are generally the compounds of the above formula wherein R, R', Q, and Q' are independently selected from alkyl groups containing 1-6 carbons.

Conjugated dienes that can be reacted with the 4-aminomethylphenols are generally compounds corresponding to the formula $CHR_1=CR_2—CR_3=CHR_4$ wherein $R_1$, $R_2$, $R_3$, and $R_4$ are independently selected from hydrogen and alkyl, cycloalkyl, and aralkyl groups containing 1-8 carbons. The diene that is preferred varies with the particular end product desired but is generally 1,3-butadiene. Other suitable dienes include, e.g., 2-methyl-1,3-butadiene, 2,3-dimethyl-1,3-butadiene, 2,3-diethyl-1,3-butadiene, 2,3-dipentyl-1,3-butadiene, 1,3-pentadiene, 1,3-hexadiene, 1,3-octadiene, 2,4-hexadiene, 2,4-heptadiene, 3,5-octadiene, 2-methyl-1,3-pentadiene, 2,3-dimethyl-1,3-pentadiene, 3-methyl-2,4-hexadiene, 3,4-dimethyl-2,4-hexadiene, 4-methyl-3,5-octadiene, 4,5-dimethyl-3,5-octadiene, 1-phenyl-1,3-butadiene, 2-phenyl-1,3-butadiene, 1,4-diphenyl-1,3-butadiene, 1-phenyl-1,3-pentadiene, 1-phenyl-1,3-hexadiene, 1-phenyl-1,3-heptadiene, 1-phenyl-1,3-octadiene, 1,6-diphenyl-2,4-hexadiene, 1-cyclohexyl-1,3-butadiene, 2-cyclohexyl-1,3-butadiene, 2,3-dicyclohexyl-1,3-butadiene, etc. Ordinarily, the amount of conjugated diene employed is in the range of about 1-10 mols per mol of the 4-aminomethylphenol.

Solvents employed in the practice of the invention may be any solvents that are inert under the reaction conditions but are generally aprotic solvents. Such solvents include, e.g., hydrocarbons, especially aromatic hydrocarbons such as benzene, toluene, etc.; halogenated hydrocarbons such as tetrachloroethane, chlorinated benzenes and toluenes, etc.; lower alkanols such as methanol, ethanol, t-butyl alcohol, isohexyl alcohol, etc.; dipolar aprotic solvents such as dimethyl sulfoxide, N,N-dimethylformamide, etc. Among the preferred solvents are ethyl acetate and aromatic hydrocarbons.

The reaction is conducted by combining the components of the reaction mixture and heating them at a temperature of at least about 190° C. for a time sufficient to provide the desired product in good yield, usually about 4-30 hours. When reaction temperatures above the boiling point of the conjugated diene are utilized, the reaction is conducted under pressure, e.g., a pressure of about 10-1000 psig, to prevent volatilization; and temperatures higher than about 500° C. are generally avoided to prevent excessive decomposition of the reactants. It is generally preferred to conduct the reaction under substantially anhydrous conditions to optimize the reaction rate and yield.

The process of the invention, like the process of Roper, results in the formation of spiro[5.5]undeca-1,4,8-trien-3-ones which generally correspond to one of the formulas:

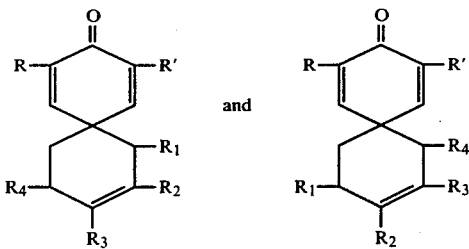 and wherein R, R'. $R_1$, $R_2$, $R_3$, and $R_4$ have the same meanings as those given above. It is an advantage of this invention that these products are prepared without the aid of an alkyl halide reactant.

The following examples are given to illustrate the invention and are not intended as a limitation thereof.

EXAMPLE I

A 300 mL Parr autoclave was charged with a solution of 10.52 g (40 mmols) of N,N-dimethyl-4-aminomethyl-2,6-di-t-butylphenol in 90 g of toluene, sealed and evacuated by a water aspirator, and then charged with 4.38 g (80 mmols) of 1,3-butadiene. The reaction mixture was heated to approximately 205° C. for 10 hours. A maximum pressure of 120 psig was obtained. After cooling, the reaction mixture was poured into a 500 mL separatory funnel, washed with approximately 2N HCl (1×50 mLs), water (1×50 mLs), and brine (1×50 mLs), dried over anhydrous magnesium sulfate, and concentrated in vacuo to afford 10.21 g (94% yield) of 2,4-di-t-butylspiro[5.5]undeca-1,4,8-trien-3-one as a brown solid. The brown solid was recrystallized from 80% ethanol to give the product as colorless crystals.

EXAMPLE II

Following the same general procedure as in Example I, 20 mmols of N,N-dimethyl-4-aminomethyl-2,6-di-t-butylphenol were reacted with approximately 222 mmols of 1,3-butadiene in 47 g of ethyl acetate at about 190° C. for 10 hours. As determined by GC analysis, the process resulted in a 100% yield of 2,4-di-t-butylspiro[5.5]undeca-1,4,8-trien-3-one.

EXAMPLE III

Following the same general procedure as in Example I, 40 mmols of N,N-dimethyl-4-aminomethyl-2-methyl-6-t-butylphenol were reacted with 80 mmols of 1,3-butadiene in 81 g of toluene at about 207° C. for 10 hours. The uncorrected isolated yield of 2-methyl-4-t-butylspiro[5.5]undeca-1,4,8-trien-3-one was 83%.

EXAMPLE IV

Following the same general procedure as in Example I, 5 mmols of N,N-dimethyl-4-aminomethyl-2,6-dimethylphenol were reacted with 20 mmols of 1,3-butadiene in 40 g of toluene at 189°–205° C. for six hours. GC analysis showed a 78% yield of 2,4-dimethylspiro[5.5]undeca-1,4,8-trien-3-one.

It is obvious that many variatons can be made in the products and processes set forth above without departing from the spirit and scope of this invention.

I claim:

1. A process which comprises heating a reaction mixture consisting essentially of a 4-aminomethylphenol, a conjugated diene, and an inert solvent at a temperature of at least about 190° C. so as to form a spiro[5.5]undeca-1,4,8-trien-3-one.

2. The process of claim 1 wherein the 4-aminomethylphenol is a compound corresponding to the formula:

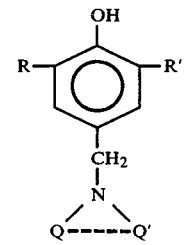

in which R and R' are independently selected from hydrogen and hydrocarbyl groups containing 1–40 carbons; and Q and Q', when separate, are independently selected from hydrogen and hydrocarbyl groups containing 1–20 carbons and, when joined together, form a ring with the nitrogen to which they are attached.

3. The process of claim 2 wherein R, R', Q, and Q' of the 4-aminomethylphenol formula are independently selected from alkyl groups containing 1–6 carbons.

4. The process of claim 1 wherein the conjugated diene is a compound corresponding to the formula $CHR_1=CR_2-CR_3=CHR_4$, in which $R_1$, $R_2$, $R_3$, and $R_4$ are independently selected from hydrogen and alkyl, cycloalkyl, and aralkyl groups containing 1–8 carbons.

5. The process of claim 4 wherein the conjugated diene is 1,3-butadiene.

6. The process of claim 1 wherein the inert solvent is an aprotic solvent.

7. The process of claim 6 wherein the solvent is an aromatic hydrocarbon.

8. The process of claim 6 wherein the solvent is ethyl acetate.

9. The process of claim 1 wherein the reaction is conducted at about 190°–500° C.

10. The process of claim 1 wherein the conjugated diene/4-aminomethylphenol mol ratio in the reaction mixture is about 1–10/1.

11. The process of claim 1 wherein a reaction mixture consisting essentially of (A) a 4-aminomethylphenol corresponding to the formula:

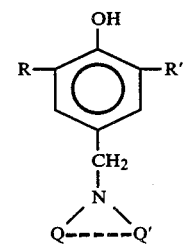

(B) a conjugated diene corresponding to the formula:

$$CHR_1=CR_2-CR_3=CHR_4$$

and (C) an inert solvent is heated at a temperature of about 190°–500° C. so as to form a spiro[5.5]undeca-1,4,8-trien-3-one; R and R' being independently selected from hydrogen and hydrocarbyl groups containing 1–40 carbons; Q and Q', when separate, being independently selected from hydrogen and hydrocarbyl groups containing 1–20 carbons and, when joined together, forming a ring with the nitrogen to which they are attached; and $R_1$, $R_2$, $R_3$, and $R_4$ being independently selected from hydrogen and alkyl, cycloalkyl, and aralkyl groups containing 1–8 carbons.

12. The process of claim 11 wherein R, R′, Q, and Q′ of the 4-aminomethylphenol formula are independently selected from alkyl groups containing 1–6 carbons, and the conjugated diene is 1,3-butadiene.

* * * * *